US00PP32788P2

(12) United States Plant Patent
Danziger

(10) Patent No.: US PP32,788 P2
(45) Date of Patent: Feb. 2, 2021

(54) ***VERBENA* PLANT NAMED 'DVERBINPR'**

(50) Latin Name: *Verbena hybrida*
Varietal Denomination: DVERBINPR

(71) Applicant: Danziger 'DAN' Flower Farm, Beit Dagan (IL)

(72) Inventor: Gavriel Danziger, Beit Dagan (IL)

(73) Assignee: Danziger "DAN" Flower Farm

( * ) Notice: Subject to any disclaimer, the term of this patent is extended or adjusted under 35 U.S.C. 154(b) by 0 days.

(21) Appl. No.: 16/873,032

(22) Filed: Jan. 16, 2020

(51) Int. Cl.
*A01H 5/02* (2018.01)
*A01H 6/86* (2018.01)

(52) U.S. Cl.
USPC ..... Plt./308
CPC ..... *A01H 6/86* (2018.05)

(58) Field of Classification Search
USPC ..... Plt./308
CPC ..... A01H 6/86
See application file for complete search history.

(56) References Cited

PUBLICATIONS

UPOV hit on *Verbena* plant named, 'DVERBINPR', CA PBR 19-10054, filed Dec. 4, 2019.*

* cited by examiner

*Primary Examiner* — Anne Marie Grunberg
(74) *Attorney, Agent, or Firm* — Cassandra Bright

(57) ABSTRACT

A new and distinct cultivar of *Verbena* plant named 'DVERBINPR' is disclosed, characterized by early flowering, an abundance of violet and white bi-color flowers, trailing habit and tolerance to powdery mildew. The new variety is a *Verbena*, normally produced as an outdoor garden or container plant.

1 Drawing Sheet

Latin name of the genus and species: *Verbena hybrida.*
Variety denomination: 'DVERBINPR'.

BACKGROUND OF THE INVENTION

The new *Verbena* cultivar is a product of a planned breeding program conducted by the inventor, Gavriel Danziger in Moshav Mishmar Hashiva, Israel. The objective of the breeding program was to produce new *Verbena* varieties. The cross resulting in this new variety was made during May of 2016.

The seed parent is the unpatented, propriety variety referred to as *Verbena* 'VE-14-7887'. The pollen parent is the unpatented, propriety variety referred to as *Verbena* 'VE-12-6806'. The new variety was discovered in November 2016 by the inventor in a group of seedlings, in a greenhouse in Moshav Mishmar Hashiva, Israel.

Asexual reproduction of the new cultivar 'DVERBINPR' first by vegetative cuttings was first performed during December of 2016, at a greenhouse in Moshav Mishmar Hashiva, Israel. Subsequent propagation by vegetative cuttings has shown that the unique features of this cultivar are stable and reproduced true to type in multiple successive generations.

SUMMARY OF THE INVENTION

The cultivar 'DVERBINPR' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DVERBINPR' These characteristics in combination distinguish 'DVERBINPR' as a new and distinct *Verbena* cultivar:

1. Early flowering.
2. Trailing habit.
3. Tolerant to powdery mildew.
4. Highly floriferous plants—abundance of bi-color violet and white flowers.

PARENT COMPARISON

Plants of the new cultivar 'DVERBINPR' are similar to plants of the seed parent, *Verbena* 'VE-14-7887' in most horticultural characteristics, however, plants of the new cultivar 'DVERBINPR' differ in the following;

1. The new variety is more vigorous than the seed parent, which has a weaker growing habit.
2. The flower color of the new variety is darker than the flower color of the seed parent.
3. The new variety is more floriferous than the seed parent.

Plants of the new cultivar 'DVERBINPR' are similar to plants of the pollen parent, *Verbena* 'VE-12-6806' in most horticultural characteristics, however, plants of the new cultivar 'DVERBINPR' differ in the following;

1. The new variety is more vigorous than the pollen parent.
2. Flowers of the new variety are a lighter violet-blue than flowers of the pollen parent.
3. The new variety is more floriferous than the pollen parent.

COMMERCIAL COMPARISON

Plants of the new cultivar 'DVERBINPR' can be compared to the unpatented commercial variety *Verbena* 'Vanessa Bicolor Purple'. These varieties are similar in most horticultural characteristics; however, 'DVERBINPR' differs in the following:

1. The new variety habit is trailing, while this comparator is semi-trailing.
2. The new variety has a darker flower color than this comparator.
3. The new variety is more vigorous than this comparator.

Plants of the new cultivar 'DVERBINPR' can also be compared to the unpatented commercial variety *Verbena* 'Vanessa Violet'. These varieties are similar in most horticultural characteristics; however, 'DVERBINPR' differs in the following:

1. The new variety habit is trailing, while this comparator is semi-trailing.
2. Flowers of the new variety are bicolored violet/white, while flowers of this comparator are solid violet.
3. The new variety is more vigorous than this comparator.

BRIEF DESCRIPTION OF THE PHOTOGRAPH

The accompanying photograph illustrates in full color a typical plant of 'DVERBINPR' grown in in a greenhouse, in Moshav Mishmar Hashiva, Israel. Age of the plant photographed is approximately 9 weeks from a rooted cutting in a 12 cm pot. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'DVERBINPR' plants grown in a nursery in Moshav Mishmar Hashiva, Israel, under natural lighting. Measurements were taken during Autumn of 2018. The plants were approximately 80 days from a rooted cutting in a 12 cm pot. The growing temperature ranged from 18° C. to 27° C. during the days, 10° C. to 15° C. during the nights. Measurements and numerical values represent averages of typical plant types.

Botanical classification: *Verbena hybrida* 'DVERBINPR'.

PROPAGATION

Time to initiate roots: 7 to 9 days at optimal temperature of approximately 23° C.

Root description: Fibrous.

PLANT

Growth habit: Trailing.

Pot size of plant described: 12 cm.

Height: 12 cm.

Plant spread: 50 cm.

Growth rate: Fast.

Branching characteristics: Freely branching.

Length of primary lateral branches: 40 cm.

Diameter of lateral branches: 0.3 cm.

Quantity of primary lateral branches: Approximately 8.

Characteristics of primary lateral branches:

- *Form.*—Cylindrical.
- *Diameter.*—0.3 cm.
- *Color.*—RHS Yellow-Green 146C.
- *Texture.*—Pubescent.
- *Strength.*—Flexible.

Internode length: 3 cm.

FOLIAGE

Leaf:

- *Arrangement.*—Opposite.
- *Quantity.*—Approximately 20 per branch.
- *Average length:* 5 cm.
- *Average width:* 3 cm.
- *Shape of blade.*—Triangular.
- *Apex.*—Acute.
- *Base.*—Acute.
- *Margin.*—Serrate.
- *Texture of top surface.*—Pubescent.
- *Pubescence.*—Strigose.
- *Aspect.*—45°.
- *Color.*—Young foliage upper side: RHS Yellow-Green 147A. Young foliage under side: RHS Yellow-Green 147B. Mature foliage upper side: RHS Green 137A. Mature foliage under side: RHS Yellow-Green 147B.
- *Venation.*—Type: Pinnate. Venation color upper side: RHS Green 138D. Venation color under side: RHS Yellow-Green 142D.
- *Petiole.*—Length: 0.5 cm. Diameter: 0.1 cm. Color: RHS Yellow-Green 147D. Texture: Pubescent.

FLOWER

Natural flowering season: Spring to Autumn under conditions found in Beit Dagan, Israel.

Days to flowering from rooted cutting: 40 to 50 days.

Inflorescence and flower type and habit: Terminal cluster.

Inflorescence size:

- *Length.*—4 to 6 cm.
- *Diameter.*—8 to 12 cm.

Rate of flower opening: 4 to 6 days from bud to fully opened flower.

Flower longevity on plant: 5 to 8 days.

Persistent or self-cleaning: Self-cleaning.

Bud:

- *Shape.*—Quinquangular.
- *Length.*—1 cm.
- *Diameter.*—0.2 cm.
- *Color.*—RHS Green 139D.

Corolla:

- *Flower.*—Depth: 3 cm. Diameter: 2 cm.
- *Petals/lobes.*—Number: 5. Length: 2 cm. Width: 1.5 cm. Shape: Obcordate. Aspect: Upright. Margin: Entire. Texture: Smooth.
- *Color.*—When opening: Upper lip: Upper surface: RHS Violet 91D. Lower surface: RHS White NN155C. Lower lip: Upper surface: RHS Violet N87A. Lower surface: RHS Violet 84D. Fully opened: Upper lip: Upper surface: RHS Violet 84D. Lower surface: RHS White NN155C. Lower lip: Upper surface: RHS Violet N87A. Lower surface: RHS Violet 84D. Throat: Color: RHS Yellow-Green 145D. Texture: Smooth. Tube color: RHS Yellow-Green 145D.

Calyx:

- *Form.*—Tubular.
- *Length.*—1 cm.
- *Diameter.*—0.2 cm.

*Sepal shape*.—Five sepals whose margins are fused-quinquangular.
*Sepal margin*.—Entire.
*Sepal texture*.—Pubescent.
*Sepal color*.—Upper surface: RHS Yellow-Green 146C. Lower surface: RHS Yellow-Green 146C.

Pedicels: None.

Fragrance: None.

REPRODUCTIVE ORGANS

Stamens:
*Number* (*per flower*): 4.
*Filament length*.—0.2 cm.
*Anthers*.—Shape: Conical. Length: 0.1 cm. Color: RHS Yellow-Green 154B.

Pollen:
*Color*.—RHS Green-Yellow 1A.
*Amount*.—Scant.

Pistils:
*Quantity per flower*.—1.
*Length*.—1.5 cm.
*Styles*.—Length: 1.5 cm.
*Color*.—RHS Yellow-Green 145D.
*Stigma*.—Shape: Ovoid. Color: RHS Yellow-Green 145A.

OTHER CHARACTERISTICS

Seeds and fruits: Low number of seeds observed.

Disease/pest resistance: Tolerant of powdery mildew.

Temperature tolerance: Tolerates temperatures from approximately −1° C. to 32° C.

What is claimed is:

1. A new and distinct cultivar of *Verbena* plant named 'DVERBINPR' as herein illustrated and described.

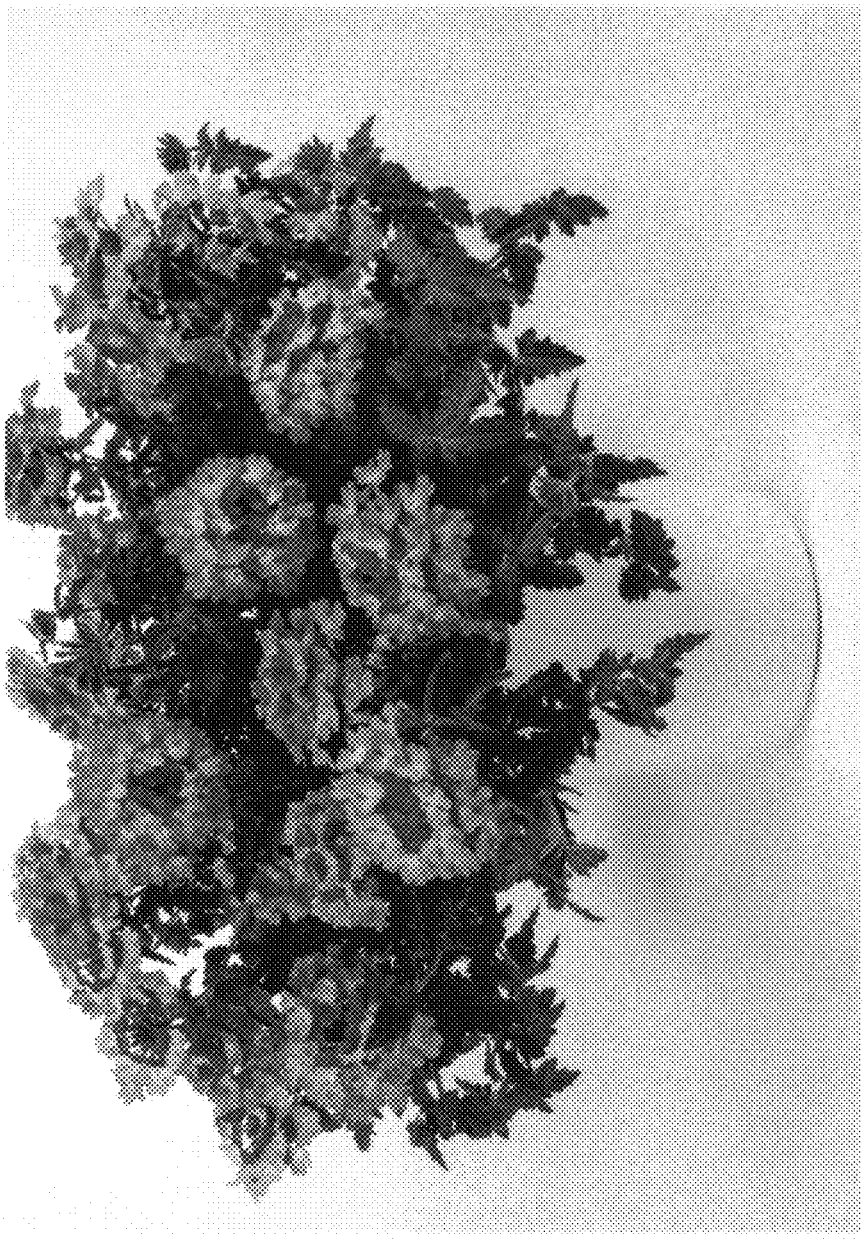

* * * * *